US009101317B2

(12) United States Patent
Kobayashi

(10) Patent No.: US 9,101,317 B2
(45) Date of Patent: Aug. 11, 2015

(54) X-RAY IMAGING APPARATUS WITH HANDLE UNIT

(75) Inventor: Kensuke Kobayashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 212 days.

(21) Appl. No.: 13/588,847

(22) Filed: Aug. 17, 2012

(65) Prior Publication Data
US 2013/0051531 A1 Feb. 28, 2013

(30) Foreign Application Priority Data

Aug. 22, 2011 (JP) ................. 2011-180636

(51) Int. Cl.
A61B 6/00 (2006.01)
G03B 42/04 (2006.01)
(52) U.S. Cl.
CPC ............. *A61B 6/4283* (2013.01); *A61B 6/4233* (2013.01); *A61B 6/467* (2013.01); *G03B 42/04* (2013.01)
(58) Field of Classification Search
CPC ...... G03B 42/02; G03B 42/025; G03B 42/04; G01T 1/003; G01T 1/023; G01T 1/026; G01T 1/08; G01T 1/16; G01T 1/20; G01T 1/2018; G01T 1/24; G01T 1/366; G01T 1/2928; G01N 23/04; A61B 6/42; A61B 6/4208; A61B 6/4216; A61B 6/4233; A61B 6/4283; A61B 6/4405; A61B 6/4429; A61B 6/46; A61B 6/4411; A61B 6/4494; H04N 5/32; H05G 1/06
USPC ............... 378/62, 87, 98, 167, 182, 189, 195, 378/102, 103
See application file for complete search history.

(56) References Cited

U.S. PATENT DOCUMENTS

| 7,696,722 | B2 | 4/2010 | Utschig et al. |
| 2005/0207534 | A1 | 9/2005 | Petrick et al. |
| 2008/0240358 | A1* | 10/2008 | Utschig et al. ................ 378/107 |
| 2009/0026378 | A1* | 1/2009 | Yoshimi et al. .......... 250/370.08 |
| 2009/0052629 | A1 | 2/2009 | Ohta et al. |

(Continued)

FOREIGN PATENT DOCUMENTS

| CN | 101493426 A | 7/2009 |
| JP | 2009237074 A | 10/2009 |
| JP | 2010-012060 A | 1/2010 |
| JP | 2010-025984 A | 2/2010 |
| JP | 2010-128469 A | 6/2010 |
| JP | 2011-112922 A | 6/2011 |
| WO | 2011/064968 A1 | 6/2011 |
| WO | WO2011064968 | * 6/2011 ............. G03B 42/04 |

OTHER PUBLICATIONS

Progress of wireless communication installation in Japanese hospitals, Eisuke Hanada and Takato Kudou, 2009, IEICE proceedings, 23S1-1, p. 554.*

Primary Examiner — Glen Kao
Assistant Examiner — Julio M Duarte-Carvajali
(74) Attorney, Agent, or Firm — Canon USA Inc. IP Division

(57) ABSTRACT

A radiation imaging apparatus includes an imaging unit and a handle unit detachably attached to the imaging unit. The imaging unit includes a digital radiation detector including a detection area, a housing incorporating the digital radiation detector, a power arranged on one side surface of the housing, and a display unit arranged on the one side surface and configured to indicate a state of the digital radiation detector. The handle unit includes a frame unit covering at least part of each of three side surfaces other than the one side surface of the housing and a grasping portion forming an opening between the handle unit and at least part of the one side surface, with the handle unit attached to the imaging unit.

15 Claims, 8 Drawing Sheets

(56) References Cited

U.S. PATENT DOCUMENTS

| | | | |
|---|---|---|---|
| 2010/0038549 A1* | 2/2010 | Nishino et al. | 250/370.09 |
| 2010/0054399 A1 | 3/2010 | Nishino et al. | |
| 2010/0111263 A1 | 5/2010 | Lamberty et al. | |
| 2010/0284521 A1 | 11/2010 | McBroom et al. | |
| 2011/0261928 A1* | 10/2011 | Ohta | 378/62 |

* cited by examiner

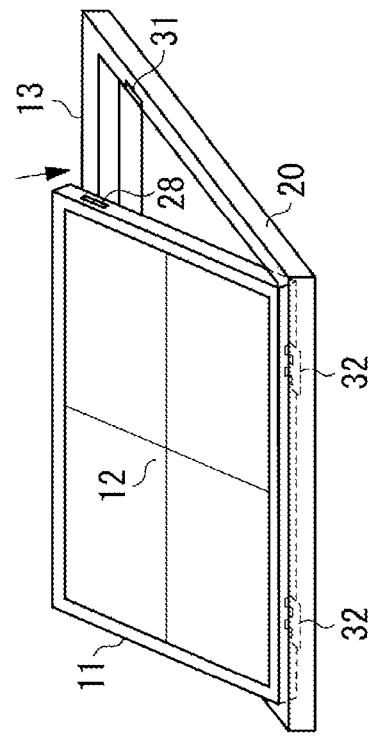
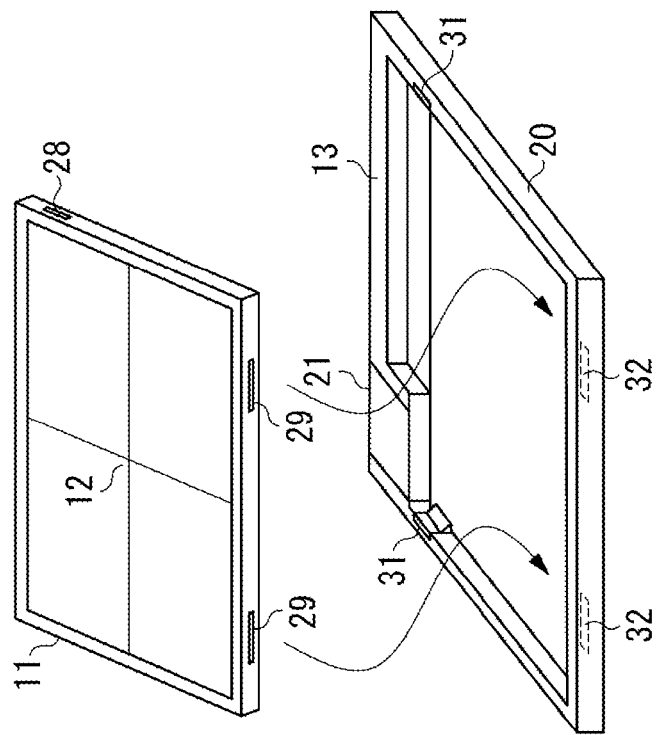
FIG. 8B
FIG. 8A

X-RAY IMAGING APPARATUS WITH HANDLE UNIT

BACKGROUND

1. Field of Invention

The present application is generally related to radiation imaging, and more particularly the present application is related to an X-ray imaging apparatus equipped with a novel handle unit.

2. Description of Related Art

X-ray imaging, an imaging technique in which a subject is irradiated with X-rays and a film-screen is used to detect the intensity distribution of the X-rays passing through the subject in order to obtain X-ray image of the object, is well known. Nowadays, the imaging method has been shifted from the conventional film-screen method to a digital radiography (DR) method using an imaging apparatus (a plat panel detector (FPD)) including a plane sensor on which pixels of minute photoelectric conversion elements and switching elements are arranged in a checkered pattern. The advantages of the DR method are that a stable X-ray image is obtained even if the amount of X-ray exposure is varied because the plane sensor in a FPD has a much wider dynamic range than a conventional photosensitive film, and that X-rays can be instantly obtained because chemical treatment is not required.

An X-ray imaging apparatus is categorized into two types: a stationary type that is installed at a predetermined location such as a general imaging chamber, and a portable type that can be carried around. In recent years, a demand for a portable X-ray imaging apparatus (hereinafter referred to as an "electronic cassette") has increased.

Furthermore, in recent years, a wireless cassette incorporating a battery and an antenna for radio communication instead of a power supply cable has been proposed by patent and non-patent literature documents, and has been made commercially available.

Japanese Patent Application Laid-Open No. 2009-237074 (herein JP 2009-237074), and U.S. Patent Application Publication No. 2010/0054399 (herein US 2010/0054399) discuss a wireless cassette provided with a handle portion to improve portability. In JP 2009-237074, a detachable grip member is provided with an antenna along an outer surface therein. In US 2010/0054399 a handle portion has a notification section that gives notice of an operating state of the radiation detector. Further, U.S. Pat. No. 7,696,722 discloses a detachable handle for a wireless X-ray detector; a power level indicator is provided on the outer surface of the handle. However, if a shielding substance adheres to grip member of the electronic cassette discussed in Japanese Patent Application Laid-Open No. 2009-237074, the strength of a radio wave is lowered; moreover, when the grip member is grasped by the operator, radio communication is blocked. In addition, although a unit for notifying an operator of the state of the electronic cassette is provided on the handle of the electronic cassette discussed in US 2010/0054399, the state notification can covered when the operator grasps the handle. A similar problem exists with U.S. Pat. No. 7,696,722.

SUMMARY

According to at least one embodiment of the present invention, a radiation imaging apparatus includes an imaging unit and a handle unit detachably attached to the imaging unit. The imaging unit includes a digital radiation detector including a detection area, a housing incorporating the digital radiation detector, a power switch arranged on one side surface of the housing, and a display unit arranged on the one side surface and configured to indicate a state of the digital radiation detector. The handle unit includes a frame unit covering at least part of each of three side surfaces other than the one side surface of the housing, and a grasping portion forming an opening between the handle unit and at least part of the one side surface, with the handle unit attached to the imaging unit. The power switch and the display unit are arranged in a position surrounding the opening on a side surface other than the grasping portion.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 8A and 8B are front views of the X-ray imaging apparatus and the detachable frame in an attachment state and in a detachment state.

DESCRIPTION OF THE EMBODIMENTS

Various exemplary embodiments, features, and aspects of the invention will be described in detail below with reference to the drawings.

Figure 1A:
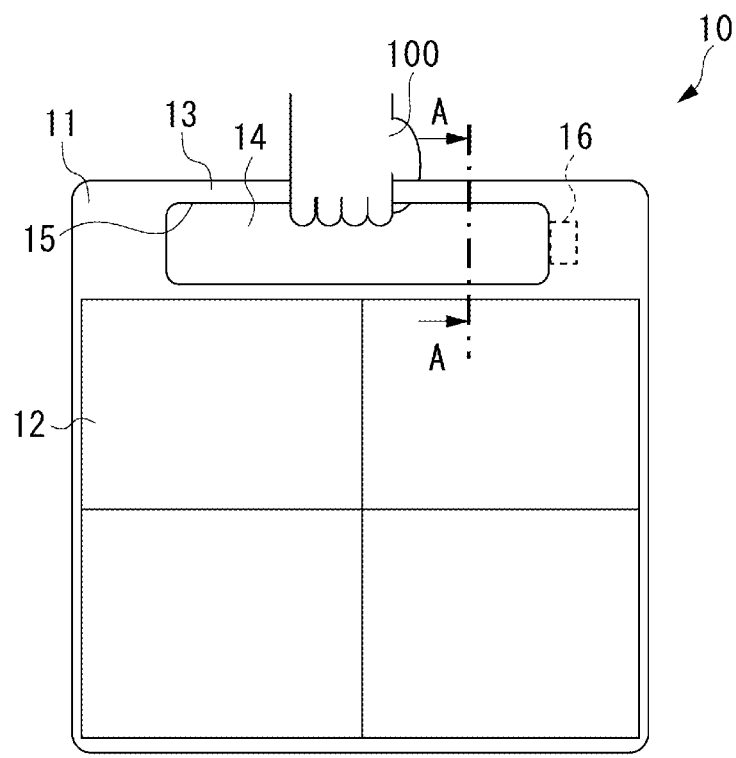
FIGS. 1A and 1B respectively illustrate a front view and a cross-section view of an X-ray imaging apparatus according to an exemplary embodiment of the present invention.
Figure 1B:
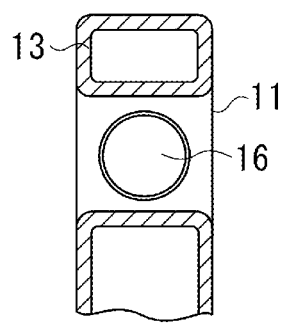
Figure 2A:
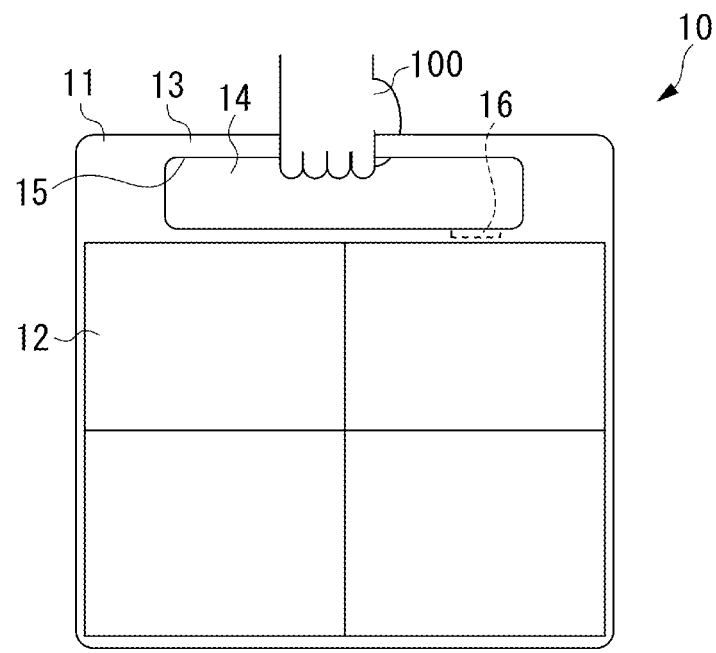
FIGS. 2A and 2B respectively illustrate a front view and a perspective view of the X-ray imaging apparatus according to a modified example of an exemplary embodiment.
Figure 2B:
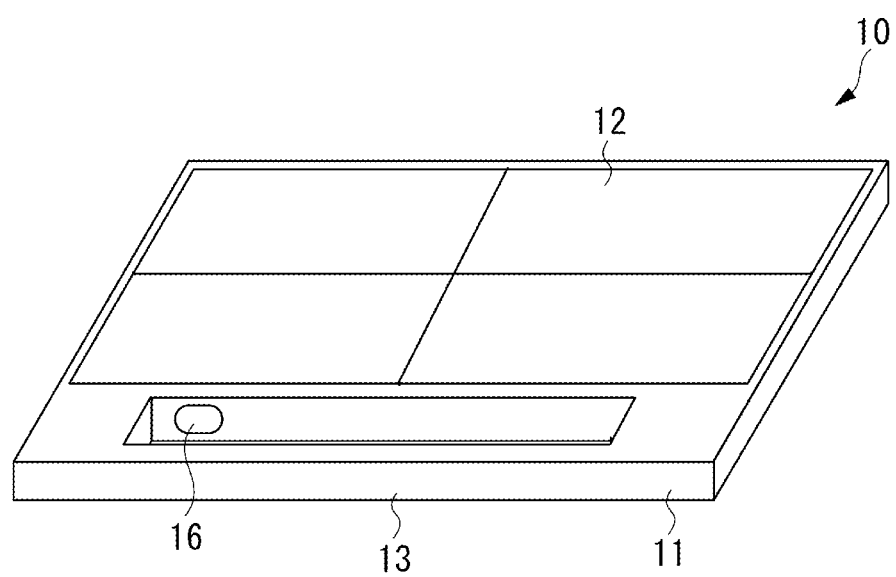

FIG. 1A is a front view of an X-ray imaging apparatus (hereinafter referred to as electronic cassette 10) according to an exemplary embodiment. FIG. 1B is a cross-section view taken along line A-A in the electronic cassette 10 according to an exemplary embodiment. FIGS. 2A and 2B are a front view and a perspective view of the electronic cassette 10 according to a modified example of an exemplary embodiment, respectively.

An X-ray sensor housing 11 of the electronic cassette 10 is configured to be held by an operator's hand 100. As illustrated in FIG. 1A, the operator's hand 100 grasps a grasping portion of the handle unit 13, by placing the operators fingers into an opening 14 of the handle unit 13. More specifically, the handle unit 13 includes a frame unit, namely the frame formed by the portion grasped by the operator's hand and the surfaces orthogonal thereto. Thus, the grasping portion forms an opening between the frame unit and at least part of one side surface of the sensor housing 11, when the handle unit attached to the imaging unit. A user interface (IF) portion 16 is arranged on a position other than the grasping portion, so that the operator's hand does not interfere with the visibility or operation of the IF portion 16. Notably, the IP portion 16 is arranged on a position other than positions on external side surfaces of the housing including an X-ray radiation surface 12 having a rectangular effective area of a sensor unit and an internal side surface 15 of the handle's grasping portion to be grasped by the operator's hand 100. The user IF portion 16 is formed of a button for turning on/off a power supply (power switch), for example, and a button for selecting an imaging unit to be used for imaging. This structure can prevent the user IF portion 16 from being operated at the operator's unintended timing or being damaged due to some external force. Even in a case where another object is provided in contact with the external side surface of the handle unit 13, the operation space of the user IF portion 16 can be secured by the opening 14 of the handle unit.

In the electronic cassette 10 illustrated in FIGS. 1A and 1B, the user IF portion 16 is arranged on the internal side surface of the opening adjacent to the internal side surface 15 of the handle. Because the operator's hand grasps the center portion of the handle 13 in order to keep the electronic cassette 10 well balanced, the operator's hand is far away from the user IF portion 16 to substantially improve the effect of avoiding erroneous operation.

In the electronic cassette 10 illustrated in FIGS. 2A and 2B, the user IF portion 16 is arranged on the internal side surface of the opening opposite the internal side surface 15 of the handle. The electronic cassette 10 illustrated in FIGS. 2A and 2B is different to the electronic cassette 10 illustrated in FIGS. 1A and 1B in that the user IF portion 16 is accessible to the operator when inserting the electronic cassette 10 into a stand or a bed.

Figure 3A:
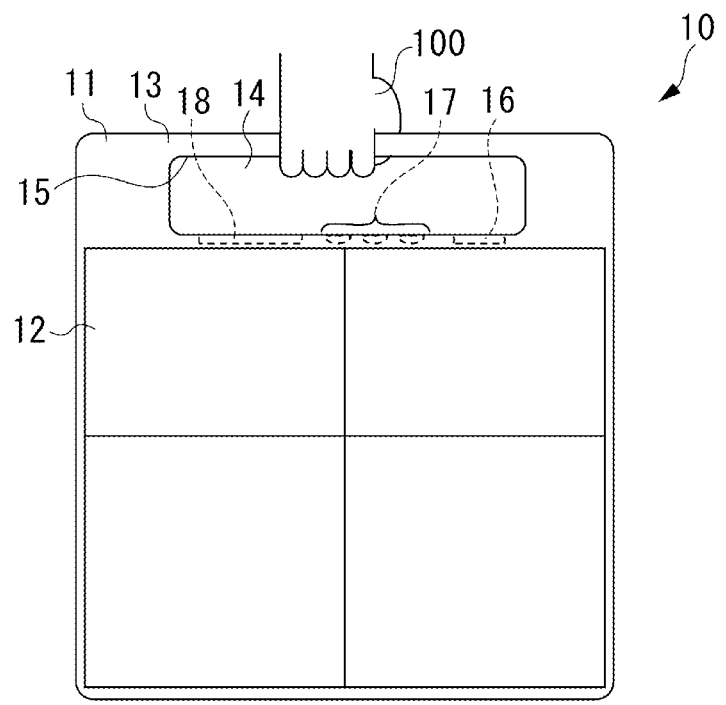
FIGS. 3A and 3B respectively illustrate a front view and a perspective view of the X-ray imaging apparatus according to another exemplary embodiment.
Figure 3B:
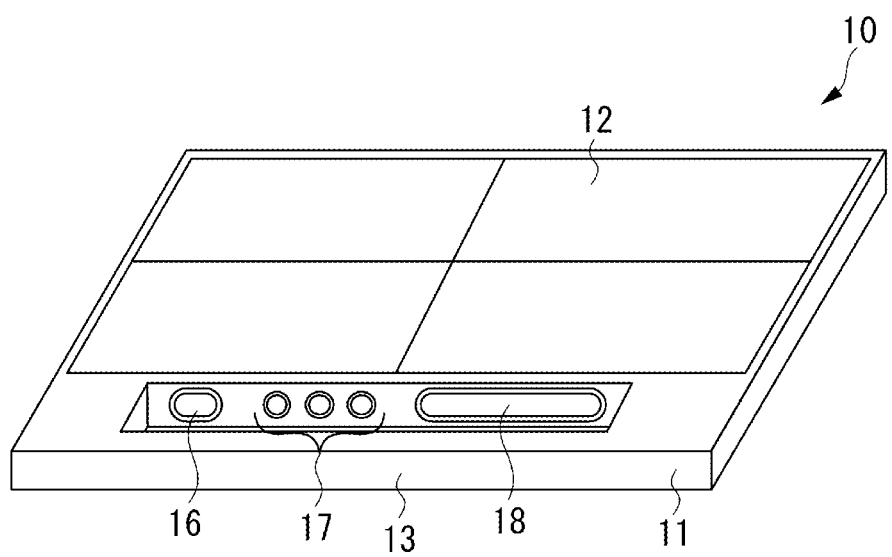

FIGS. 3A and 3B are respectively a front view and a perspective view of the electronic cassette 10 according to another exemplary embodiment. A status display unit 17 for indicating the status of the electronic cassette 10 (power supply, state of a sensor, and remaining built-in battery capacity) and a radio wave radiation window 18 for an antenna used for radio communication with an external control unit (not illustrated) are arranged side by side on the internal side surface of the opening where the user IF portion 16 is arranged. The radio wave radiation window 18 is the one that the side surface of the metallic X-ray sensor housing 11 is partly opened and another member made of a radio-wave transmissive resin is fitted into the portion that is partially opened. If the radio wave radiation window 18 is covered with a shielding substance such as a hand, it becomes impossible to communicate wirelessly because the radio wave cannot pass through the radio wave radiation window 18.

The present exemplary embodiment not only secures space for operating the user IF portion 16, described in the exemplary embodiment, but also allows easy access so that the user can check the state of the electronic cassette 10 even with the handle 13 grasped and stable transmission and reception are enabled because the radio wave radiation window 18 is free from obstructive interference. Furthermore, the above three elements are arranged on the same side surface as the handle 13 or in the same direction of the X-ray sensor housing 11 to eliminate the need for arranging members on the other three side surfaces. Therefore, the distance from the contour of the housing to the end of effective pixels of the built-in X-ray sensor can be reduced to the minimum necessary distance at which the strength of the housing can be secured. This enables shooting with the three side surfaces brought in close contact with a desired portion.

Figure 4A:
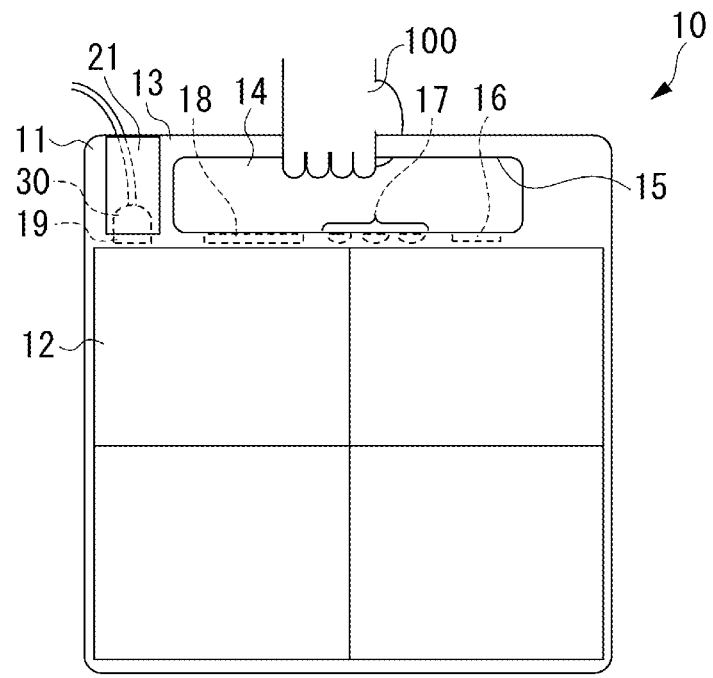
FIGS. 4A and 4B respectively illustrate a front view and a perspective view of the X-ray imaging apparatus according to another exemplary embodiment.
Figure 4B:
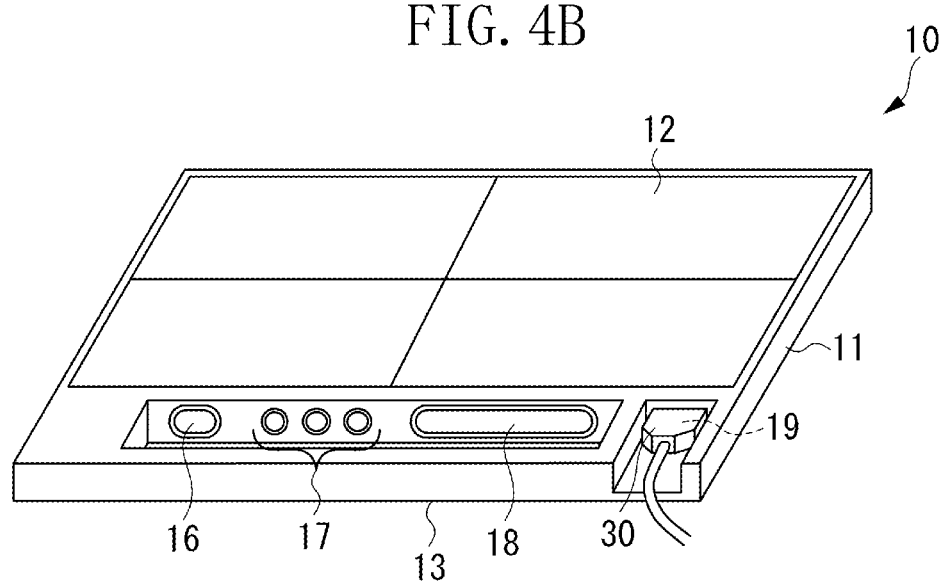

FIGS. 4A and 4B are respectively a front view and a perspective view of the electronic cassette 10 according to a further exemplary embodiment. The electronic cassette 10 according to this exemplary embodiment is different from the electronic cassette 10 illustrated in FIGS. 3A and 3B in that the electronic cassette 10 of this embodiment is connected to an external control unit (not illustrated) via a cable. More specifically, the present exemplary embodiment includes a connector (a connection unit) 19 detachably connected with a cable which is supplied with power from an external apparatus or is used for communicating with an external control unit via the cable.

In a clinical site, radio communication sometimes cannot be made due to obstruction caused by the subject being imaged, or due excessive RF interference in the imaging environment. Even in such a case, the electronic cassette 10 of the present exemplary embodiment can perform normal shooting because the connector 19 can be easily accessed from the same direction as the status display unit 17. For example, when the electronic cassette 10 transmits a captured image to an external control unit, the communication connection should not be interrupted. In such a case, the status display unit 17 displays a message not to detach an external connecter 30 from the connector 19, thereby allowing the operator's attention to be attracted.

Although not displayed in FIG. 4B for the sake of convenience, the opening from the connector 19 to the contour of the X-ray sensor housing 11 is covered with a lid member 21 to make a space for routing the external connecter 30 and cable a structurally strong airtight space.

Thus, the connector 19 is not subjected to a bending load in the width direction of the housing, and this reduces the risk of damaging the connector 19. However, to secure a sufficient strength, the connector needs to be protruded to some extent from the substantial contour of the built-in X-ray sensor. It is effective to arrange the connector 19 and the handle 13 side by side in that the three other side surfaces can be made close to the contour of the built-in X-ray sensor as much as possible. This is because shooting is enabled with the side surfaces brought into close contact with a desired portion, as described in the exemplary embodiment.

Figure 5A:
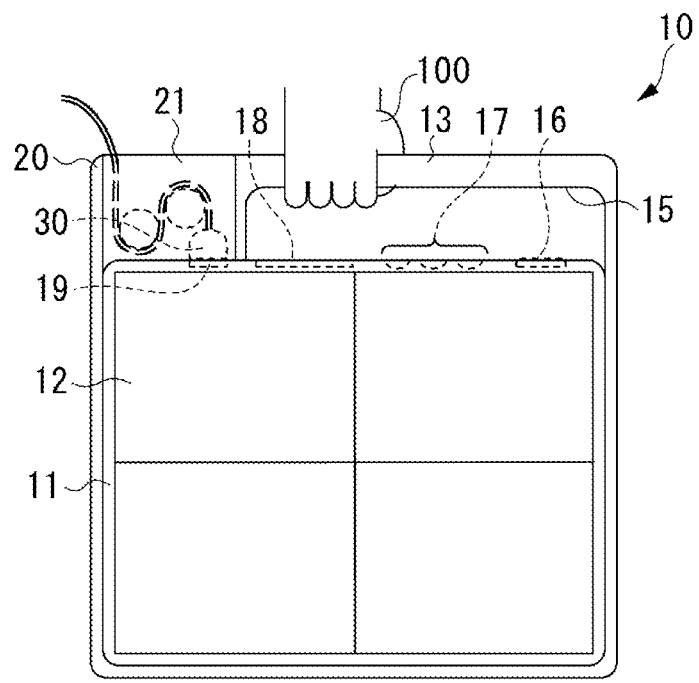
FIGS. 5A and 5B respectively illustrate a front view and a perspective view of the X-ray imaging apparatus according to another exemplary embodiment.
Figure 5B:
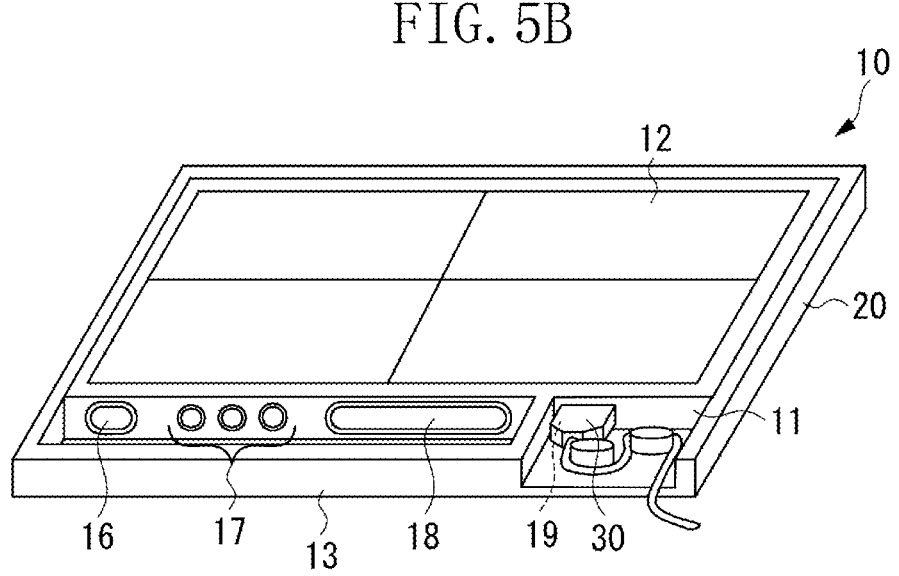

FIGS. 5A and 5B are respectively a front view and a perspective view of the electronic cassette (radiation imaging apparatus) 10 according to yet another exemplary embodiment. In the electronic cassette 10 according to the present exemplary embodiment, a frame 20 with a handle (a handle unit) is detachably attached to an imaging unit including the X-ray sensor housing 11 incorporating the X-ray sensor. The X-ray sensor housing 11 is substantially of a rectangular parallelepiped shape and substantially agrees with a film cassette in size, so that the X-ray sensor housing 11 can be directly attached to a frame (a stand device) produced for the film cassette.

The user IF portion 16, the status display unit 17 for indicating the status of the electronic cassette 10 or the X-ray sensor, the radio wave radiation window 18, and the connector 19 with which the external connecter 30 engages are all arranged on one side surface adjacent to the X-ray radiation surface 12 of the X-ray sensor housing 11. The user who does not need the handle can make the electronic cassette 10 the one that has minimum necessary configuration and weight to fulfill a shooting function.

An antenna for emitting radio waves via the radio wave radiation window 18 and the connector 19 are arranged on the same edge. This can simplify wirings to connect each portion with a control unit (not illustrated) incorporated in the X-ray sensor housing 11, which is superior in reducing the weight of components and the number of components, and in facilitating the assembly.

Figure 7:
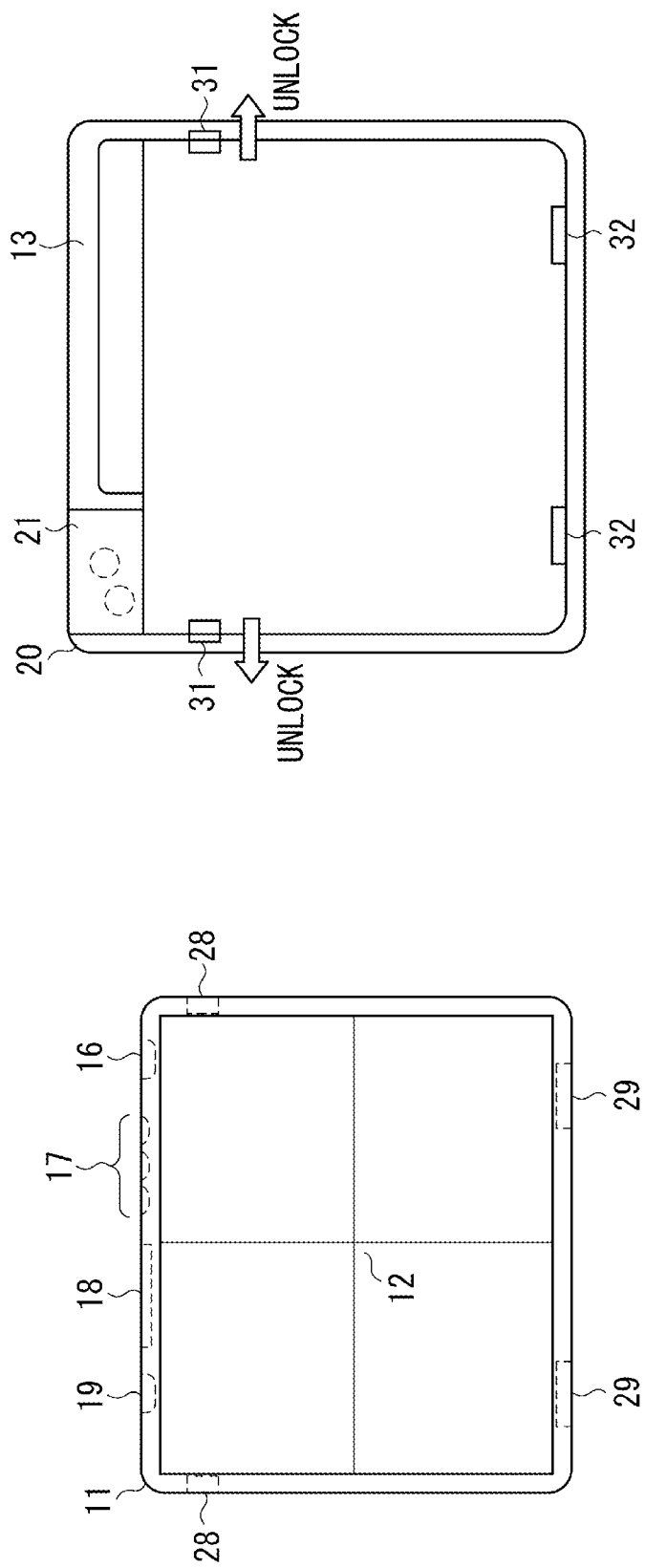
FIG. 7 is a front view of the X-ray imaging apparatus and the detachable frame in accordance with another embodiment of the present invention.

Notches on the metallic housing including the radio wave radiation window 18 do not need to be provided on three faces of the X-ray sensor housing 11. This can reduce decrease in strength caused by the notches to a minimum level as the entire housing. As shown in FIG. 7, the frame 20 includes a plurality of lock mechanisms 31 and hooks 32 fixed on the side surface of the frame 20, corresponding to a plurality of look recesses 28 and a plurality of hook recesses 29 provided inwardly on the side surface of the X-ray sensor housing. They enables the X-ray detector housing 11 and the frame to be detachably attached together. The lock mechanism 31 includes a spring fixed at one end on the frame 20 and a stop member attached to the other end of the spring. By the spring the stop member can be moved to a direction inwardly into side surface of the spring. When the stop member pushed, the stop member is moved into the frame 20. As shown in FIG. 8A, When attaching the frame 20 with the X-ray detector housing 11, hook recess 29 is hooked up to the hook 32. And as shown in FIG. 8B, the X-ray detector housing 11 is moved to a direction shown in FIG. 8B with an arrow, so that a surface of the X-ray detector housing facing away with the X-ray radiation surface 12 is brought close to the frame 20. By the move the lock recess 28 is hooked up to the stop member of the lock mechanism 31, and the attachment is completed. On the other hand when the frame 20 is detached from the X-ray detector housing 11, the X-ray detector 11 is taken away from the frame 20, with the stop members of the lock mechanism 31 pushed into the frame 20. And the attachment between the hooks 32 and the hook recesses 29 are released by moving the X-ray detector 11 away from the frame 20. The lid member 21 and the frame 20 with the handle function as a protection portion for protecting the connector 19. The protection portion prevents the connected cable from being detached when the frame 20 with the handle is attached to the imaging unit (the X-ray sensor housing 11).

When the X-ray sensor housing 11 is fixed, the cable of the external connecter 30 attached to the connector 19 on the X-ray sensor housing 11 is pulled around to be fixed. Thus, even if the cable is pulled, a tensile force is not directly applied to the external connecter 30.

The three side surfaces except one side surface of the X-ray sensor housing 11 on which the user IF portion 16 is provided are covered with the frame to increase strength. Further, the opening from the connector 19 to the contour of the frame 20 with the handle is covered with the lid member 21 (not illustrated in the perspective view), thus substantially sealing a space for pulling around the external connecter 30 and the cable to increase the structural strength of the space. Thereby, the connector 19 is not directly or hardly subjected to a bending load in all directions so that the risk of damaging the connector 19 can be reduced.

On the other hand, the user IF portion 16, the status display unit 17, and the radio wave radiation window 18 face the internal side surface 15 of the handle with only the space into which the operator's hand 100 is put, thereby being protected from an external force by the handle 13. When the frame 20 with the handle is attached to the imaging unit (the X-ray sensor housing 11), an opening by the side surfaces of the frame 20 with the handle and the X-ray sensor housing 11 is formed. The user IF portion 16, the status display unit 17, and the radio wave radiation window 18 are arranged in a position surrounding the opening.

At the same time, operation space of the user IF portion 16, visibility of the status display unit 17, and radio wave radiation space of the radio wave radiation window 18 are all secured. The connector 19 can be accessed from the same direction as the status display unit 17. For example, when the electronic cassette 10 transmits a captured image to an external control unit, the communication connection should not be interrupted. In such a case, the status display unit 17 displays a message not to detach an external connecter 30 from the connector 19, thereby allowing the operator's attention to be attracted.

Figure 6A:
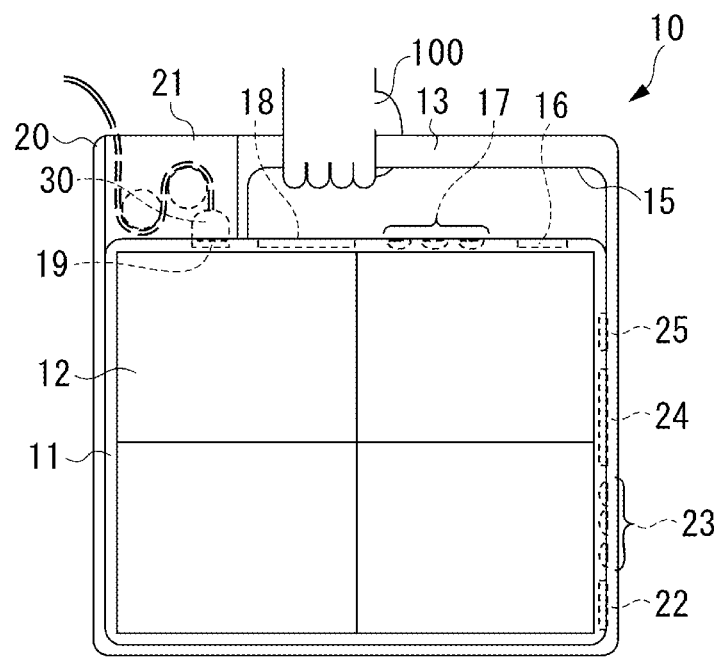
FIGS. 6A and 6B respectively illustrate a front view and a perspective view of the X-ray imaging apparatus according to yet another exemplary embodiment of the present invention.
Figure 6B:
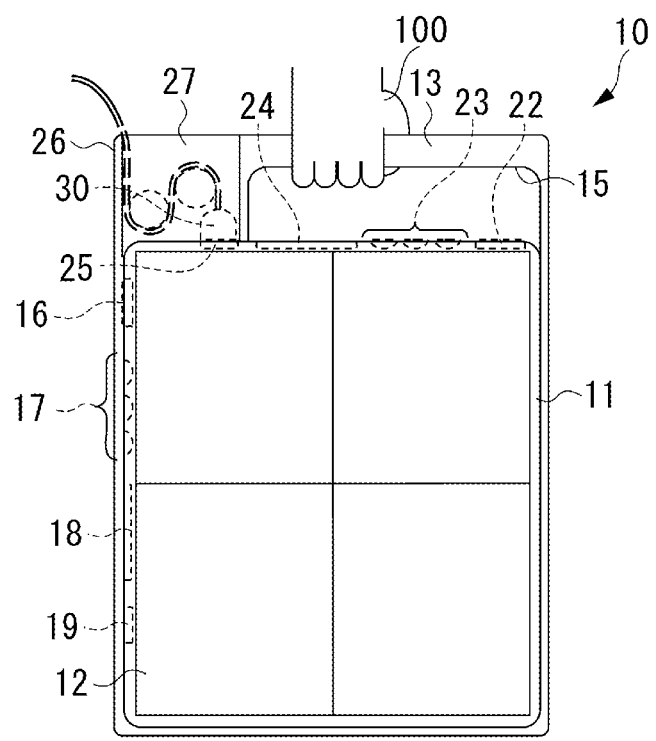

FIGS. 6A and 6B are respectively a front view and a perspective view of the electronic cassette 10 according to another exemplary embodiment. The electronic cassette 10 according to the present exemplary embodiment includes the user IF portions 16 and 22, the status display units 17 and 23 of the electronic cassette 10, the radio wave radiation windows 18 and 24, and the connectors 19 and 25 on the two orthogonal side surfaces of the X-ray sensor housing 11 respectively. The members for improving the detachable portability of the X-ray sensor housing 11 include a frame 20 with a handle in which the long side surface of the X-ray sensor housing 11 faces the handle 13 illustrated in FIG. 6A and a frame 26 with a handle in which the short side surface of the X-ray sensor housing 11 faces the handle 13 illustrated in FIG. 6B. Therefore, the frames 20 and 26 can be attached to the X-ray sensor housing 11 according to an imaging portion or an orientation.

Either of the above two frames with the handles is attached to the X-ray sensor housing 11. Then, a control unit (not illustrated) built in the X-ray sensor housing 11 makes inoperable the user IF portion, the status display unit, the radio wave radiation window, and a wire-connection connector which are arranged on the side surface that does not face the handle 13, among the side surfaces of the X-ray sensor housing 11. This prevents the user IF portion from being erroneously operated, and also prevents an antenna and the status display unit, which are blocked by the side surface of the frame, from being supplied with power to reduce wasteful power consumption. The side surface subjected to an energizing control may be determined by detecting a radio communication state to specify the side surface facing the handle 13. Alternatively, the wire-connection connector to which the external connector 30 is attached or the user IF portion which is continuously operated twice in a predetermined time period may be detected to specify the side surface facing the handle 13, or a protrusion or a marker provided on the side surface of the frame may be detected to specify the side surface facing the side surface of the frame.

The implementation of the present invention has been described above along with various exemplary embodiments, but modifications can be made within the scope of the embodiments of the present invention. For example, in the exemplary embodiments, a configuration is described in which the X-ray sensor housing is detachably attached to the frame with the handle. However, aside from the above, the X-ray sensor housing may be detachably attached to the handle itself.

While the embodiments of the present invention have been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-180636 filed Aug. 22, 2011, which is hereby incorporated by reference herein in its entirety.

What is claimed is:

1. A radiation imaging apparatus comprising:
an imaging unit; and
a handle unit detachably attached to the imaging unit,
wherein the imaging unit includes:
a digital radiation detector including a detection area;
a housing incorporating the digital radiation detector;
a power switch arranged on one side surface of the housing; and
a display unit arranged on the one side surface and configured to indicate a state of the digital radiation detector,
wherein the handle unit includes:
a frame unit covering at least a part of each of three side surfaces of the housing other than the one side surface of the housing; and
a grasping portion forming an opening between the frame unit and at least part of the one side surface with the handle unit attached to the imaging unit, and
wherein the power switch and the display unit are arranged in a position surrounding the opening on the one side surface.

2. The radiation imaging apparatus according to claim 1, wherein the imaging unit further includes:
a radio communication unit; and
a radio wave radiation window arranged on the one side surface, and
wherein the radio wave radiation window is arranged in a position surrounding the opening on the one side surface.

3. The radiation imaging apparatus according to claim 1, wherein the imaging unit further includes:
a connector unit configured to detachably connect a cable with an external apparatus, and
wherein the handle unit further includes:
a protection unit configured to cover the connector unit.

4. The radiation imaging apparatus according to claim 3, wherein the protection unit of the handle unit prevents the cable connected to the imaging unit from being detached, with the handle unit attached to the imaging unit.

5. The radiation imaging apparatus according to claim 3, wherein the protection unit of the handle unit includes a reduction mechanism configured to reduce a bending load applied to the connector, with the handle unit attached to the imaging unit.

6. A handle unit configured to be attached to an imaging unit, the imaging unit including a housing, a display unit and a power switch being arranged on one side surface of the housing, the handle unit comprising:
a frame unit covering at least part of each of three side surfaces of the housing other than the one side surface of the housing; and
a grasping portion forming an opening between the frame unit and at least part of the one side surface, with the handle unit attached to the imaging unit, and
wherein the grasping portion provides the opening so that the power switch and the display unit are arranged on the one side surface inside the opening.

7. The handle unit according to claim 6, further comprising a connector provided on the imaging unit and detachably connected to a cable via which the imaging unit connects to an external apparatus.

8. The handle unit according to claim 7, further comprising a protection unit configured to cover the connector,
wherein the protection unit prevents the cable connected to the imaging unit from being detached, with the handle unit attached to the imaging unit.

9. The handle unit according to claim 8, wherein the protection unit includes a reduction mechanism configured to reduce a bending load applied to the connector, with the handle unit attached to the imaging unit.

10. An X-ray imaging apparatus comprising:
a housing including a radiation incident surface and a side surface adjacent to the radiation incident surface;
a sensor unit enclosed in the housing, the sensor unit having an effective area for detecting X-rays;
a handle configured to be grasped by an operator to handle the X-ray imaging apparatus, the handle being detachably attached to the housing, wherein, when the handle is attached, the handle is arranged along the side surface and a grasp opening is formed between the handle and the side surface; and
a frame with which the handle is formed, the frame being configured to detachably attach to the housing and to surround the housing when attached thereto,
wherein the grasp opening is formed by a side surface of the handle, the side surface of the housing and a side surface of the frame, and
wherein at least one of an interface unit operated by the operator to control the sensor unit, a radio wave radiation window used for the sensor unit communicating with an external apparatus wirelessly, and a display unit indicating a state of the sensor unit, is arranged on the side surface of the housing, which is an inner side surface of the grasp opening.

11. The X-ray imaging apparatus according to claim 10, further comprising:
a connector arranged on the side surface of the housing along which the handle unit is provided, the connector being detachably connected with a cable externally supplied with power and used for communicating with an external control unit.

12. The X-ray imaging apparatus according to claim 10, wherein the sensor unit includes, on two orthogonal side surfaces among four side surfaces, at least one of the interface unit, the radio wave radiation window, the display unit, or a connection unit detachably connected with a cable externally supplied with power and used for communicating with an external control unit, and
wherein the sensor unit operates only one of the interface unit, the radio wave radiation window, the display unit, or the connection unit which are provided on the side surface of the housing adjacent to the handle, with the sensor unit attached to the handle unit or the frame.

13. The X-ray imaging apparatus according to claim 10, comprising:
an interface unit operated by the operator to control the sensor unit;
a radio wave radiation window used for the imaging unit communicating with an external apparatus wirelessly; and
a display unit indicating a state of the sensor unit,
wherein the interface unit, the radio wave radiation window and the display unit are arranged on the side surface of the housing.

14. The X-ray imaging apparatus according to claim 10, comprising the interface unit operated by the operator to control the sensor unit, arranged on the side surface of the housing, which is an inner side surface of the grasp opening.

15. An X-ray imaging apparatus comprising:
- a housing including a radiation incident surface and a side surface adjacent to the radiation incident surface;
- a sensor unit enclosed in the housing, the sensor unit having an effective area for detecting X-rays;
- a handle configured to be grasped by an operator to handle the X-ray imaging apparatus, the handle being detachably attached to the housing, wherein, when the handle is attached, the handle is arranged along the side surface and a grasp opening is formed between the handle and the side surface; and
- a frame with which the handle is formed, the frame being configured to detachably attach to the housing and to surround the housing when attached thereto,
- wherein the grasp opening is formed by a side surface of the handle, the side surface of the housing and a side surface of the frame, and
- wherein at least one of a radio wave radiation window used for the sensor unit communicating with an external apparatus wirelessly, and a display unit indicating a state of the sensor unit, is arranged on the side surface of the housing, which is an inner side surface of the grasp opening.

\* \* \* \* \*